United States Patent
Reich et al.

(10) Patent No.: US 11,952,375 B2
(45) Date of Patent: *Apr. 9, 2024

(54) CRYSTALLINE FORMS OF MNK INHIBITORS

(71) Applicant: eFFECTOR Therapeutics Inc., San Diego, CA (US)

(72) Inventors: Siegfried H. Reich, La Jolla, CA (US); Paul A. Sprengeler, Escondido, CA (US); Stephen E. Webber, San Diego, CA (US); Alan X. Xiang, Irvine, CA (US); Justin T. Ernst, San Diego, CA (US); Bennett C. Borer, San Diego, CA (US); Samuel Sperry, Encinitas, CA (US); Jo Ann Z. Wilson, San Francisco, CA (US)

(73) Assignee: eFFECTOR Therapeutics Inc., San Diego, CA (US)

( * ) Notice: Subject to any disclaimer, the term of this patent is extended or adjusted under 35 U.S.C. 154(b) by 170 days.

This patent is subject to a terminal disclaimer.

(21) Appl. No.: 17/484,564

(22) Filed: Sep. 24, 2021

(65) Prior Publication Data
US 2022/0119387 A1    Apr. 21, 2022

Related U.S. Application Data

(63) Continuation of application No. 16/661,507, filed on Oct. 23, 2019, now Pat. No. 11,130,757.

(60) Provisional application No. 62/749,820, filed on Oct. 24, 2018.

(51) Int. Cl.
  *C07D 471/04*    (2006.01)
  *A61K 31/506*    (2006.01)
  *A61P 35/00*    (2006.01)

(52) U.S. Cl.
  CPC ........ *C07D 471/04* (2013.01); *C07B 2200/13* (2013.01)

(58) Field of Classification Search
  CPC ...... C07D 471/04; A61K 31/506; A61P 35/00
  See application file for complete search history.

(56) References Cited

U.S. PATENT DOCUMENTS

| | | | |
|---|---|---|---|
| 5,491,144 | A | 2/1996 | Trinks et al. |
| 8,637,525 | B2 | 1/2014 | Boy et al. |
| 9,382,248 | B2 | 7/2016 | Reich et al. |
| 9,382,255 | B2 | 7/2016 | Klar et al. |
| 9,669,031 | B2 | 6/2017 | Reich et al. |
| 9,814,718 | B2 | 11/2017 | Reich et al. |
| 10,000,487 | B2 | 6/2018 | Sprengeler et al. |
| 10,112,955 | B2 | 10/2018 | Sprengeler et al. |
| 10,702,526 | B2 | 7/2020 | Webster et al. |
| 10,780,119 | B2 | 9/2020 | Webster et al. |
| 11,083,727 | B2 | 8/2021 | Ernst et al. |
| 11,130,757 | B2 | 9/2021 | Reich et al. |
| 2007/0219218 | A1 | 9/2007 | Yu et al. |
| 2008/0039450 | A1 | 2/2008 | Jensen et al. |
| 2010/0105708 | A1 | 4/2010 | Jaekel et al. |
| 2011/0280886 | A1 | 11/2011 | Grzmil et al. |
| 2012/0184535 | A1 | 7/2012 | Brzozka et al. |
| 2015/0038506 | A1 | 2/2015 | Nacro et al. |
| 2015/0376181 | A1 | 12/2015 | Reich et al. |
| 2016/0303124 | A1 | 10/2016 | Webster et al. |
| 2016/0317536 | A1 | 11/2016 | Reich et al. |
| 2017/0121339 | A1 | 5/2017 | Sprengeler et al. |
| 2017/0121346 | A1 | 5/2017 | Sprengeler et al. |
| 2017/0145009 | A1 | 5/2017 | Sprengeler et al. |
| 2017/0191136 | A1 | 7/2017 | Thompson et al. |
| 2017/0266185 | A1 | 9/2017 | Reich et al. |
| 2018/0085368 | A1 | 3/2018 | Reich et al. |
| 2018/0228803 | A1 | 8/2018 | Ernst et al. |
| 2018/0353545 | A1 | 12/2018 | Webster et al. |
| 2019/0209560 | A1 | 7/2019 | Reich et al. |
| 2019/0275039 | A1 | 9/2019 | Ernst et al. |
| 2020/0131179 | A1 | 4/2020 | Reich et al. |
| 2021/0338673 | A1 | 11/2021 | Reich et al. |

(Continued)

FOREIGN PATENT DOCUMENTS

| | | |
|---|---|---|
| CL | 2016003293 A1 | 9/2017 |
| CN | 101472912 A | 7/2009 |
| CN | 101511837 A | 8/2009 |

(Continued)

OTHER PUBLICATIONS

International Preliminary Report on Patentability for Application No. PCT/US2015/037416, dated Jan. 5, 2017, 7 pages.
International Preliminary Report on Patentability issued in International Application No. PCT/US2018/018022, dated Aug. 29, 2019, 8 pages.
International Search Report and Written Opinion for PCT International Application No. PCT/US2015/037416, dated Sep. 17, 2015, 8 pages.
International Search Report and Written Opinion received for PCT Application No. PCT/US19/57656, dated Feb. 21, 2020, 10 pages.
International Search Report issued in International Application No. PCT/US18/18022, dated Jun. 7, 2018, 5 pages.

(Continued)

*Primary Examiner* — Brenda L Coleman
(74) *Attorney, Agent, or Firm* — Mintz Levin Cohn Ferris Glovsky and Popeo, P.C.

(57) ABSTRACT

The present invention provides crystalline solids of 6'-((6-aminopyrimidin-4-yl)amino)-8'-methyl-2'H-spiro[cyclohexane-1,3'-imidazo[1,5-a]pyridine]-1',5'-dione:

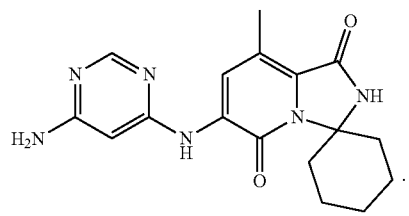

The crystalline compounds of the present application are inhibitors of Mnk and finds utility in any number of therapeutic applications, including but not limited to treatment of inflammation and various cancers.

6 Claims, 4 Drawing Sheets

(56) References Cited

U.S. PATENT DOCUMENTS

2022/0096472 A1  3/2022  Ernst et al.

FOREIGN PATENT DOCUMENTS

| | | |
|---|---|---|
| CN | 102186857 A | 9/2011 |
| CO | 2017000399 A2 | 4/2017 |
| EA | 201790078 A1 | 5/2017 |
| ES | 2359233 T3 | 5/2011 |
| JP | 2009173629 A | 8/2009 |
| JP | 2009542749 A | 12/2009 |
| JP | 6615797 B2 | 12/2019 |
| RU | 2619944 C2 | 5/2017 |
| TW | 201831479 A | 9/2018 |
| TW | 201833102 A | 9/2018 |
| WO | 02098428 A1 | 12/2002 |
| WO | 2005000385 A1 | 1/2005 |
| WO | 2005082856 A2 | 9/2005 |
| WO | 2006020879 A1 | 2/2006 |
| WO | 2006135783 A2 | 12/2006 |
| WO | 2007021309 A1 | 2/2007 |
| WO | 2007147874 A1 | 12/2007 |
| WO | 2008006547 A2 | 1/2008 |
| WO | 2008115369 A2 | 9/2008 |
| WO | 2008117061 A2 | 10/2008 |
| WO | 2009065596 A2 | 5/2009 |
| WO | 2009112445 A1 | 9/2009 |
| WO | 2010023181 A1 | 3/2010 |
| WO | 2011014535 A1 | 2/2011 |
| WO | 2011017296 A1 | 2/2011 |
| WO | 2011106168 A1 | 9/2011 |
| WO | 2012041987 A1 | 4/2012 |
| WO | 2012075140 A1 | 6/2012 |
| WO | 2013000994 A1 | 1/2013 |
| WO | 2013043192 A1 | 3/2013 |
| WO | 2013100632 A1 | 7/2013 |
| WO | 2013147711 A1 | 10/2013 |
| WO | 2013148748 A1 | 10/2013 |
| WO | 2013151975 A1 | 10/2013 |
| WO | 2013174743 A1 | 11/2013 |
| WO | 2014044691 A1 | 3/2014 |
| WO | 2014072244 A1 | 5/2014 |
| WO | 2014088519 A1 | 6/2014 |
| WO | 2014099941 A1 | 6/2014 |
| WO | 2014128093 A1 | 8/2014 |
| WO | 2015074986 A1 | 5/2015 |
| WO | 2015138839 A1 | 9/2015 |
| WO | 2015200481 A1 | 12/2015 |
| WO | 2016096721 A1 | 6/2016 |
| WO | 2016172010 A1 | 10/2016 |
| WO | 2017075394 A1 | 5/2017 |
| WO | 2017085483 A1 | 5/2017 |
| WO | 2017085484 A1 | 5/2017 |
| WO | 2018134148 A1 | 7/2018 |
| WO | 2018152117 A1 | 8/2018 |
| WO | 2019099838 A1 | 5/2019 |
| WO | 2019103926 A1 | 5/2019 |

OTHER PUBLICATIONS

Invitation to Pay Additional Fees received for PCT Patent International Application No. PCT/US19/57656, dated Dec. 26, 2019, 2 pages.
International Search Report and Written Opinion Issued in International Patent Application No. PCT/US2016/062787, dated Apr. 12, 2017, 10 pages.
(Nov. 26, 2013) Aurora Fine Chemicals "Chemical Catalog excerpt 1481116-61-3", 1 page.
(Dec. 1, 2013) Aurora Fine Chemicals "Chemical Catalog excerpt 1484631-21-1", 1 page.
(Dec. 17, 2013) Aurora Fine Chemicals "Chemical Catalog excerpt 1496979-81-7", 1 page.
(Dec. 29, 2013) Aurora Fine Chemicals "Chemical Catalog excerpt 1505663-52-4", 1 page.
(Jan. 5, 2014) Aurora Fine Chemicals "Chemical Catalog excerpt 1511646-58-4", 1 page.
Buxade et al. (Aug. 2005) "The Mnks Are Novel Components in the Control of TNFα Biosynthesis and Phosphorylate and Regulate hnRNP A1", Immunity, 23(2):177-189.
Cao et al. (Jun. 2018) "Inhibition of eIF4E Cooperates with Chemotherapy and Immunotherapy in Renal Cell Carcinoma", Clinical & Translational Oncology, 20(6):761-767.
Charrier-Savoumin et al. (2013) "p-S6RP, p-p70S6K NS P-eif4e—Validation of three new HTRF phospho-assays or the study of translational control", Cisbio Bioassays., 1 page.
Conti et al. (2001) "MCP-1 and RANTES are Mediators of Acute and Chronic Inflammation", Allergy & Asthma Proceedings, 22(3):133-137.
Diab et al. (Feb. 24, 2016) "Unveiling New Chemical Scaffolds as Mnk Inhibitors", Future Medicinal Chemistry, 8(3):271-285.
Effector Therapeutics "Globenewswire 2020", Available on https://www.globenewswire.com/news-4 elease/2020/05/29/2040865/0/en/eFFECTOR-s-Tomivosertib-Demonstrates-Positive-Phase-2-Results-for-Subjects-With-Non-Small-Cell-Lung-Cancer-in-Combination-with-Checkpoint-Inhibitors.html. 3 pages.
Fukunaga et al. (Apr. 15, 1997) "MNK1, a New MAP Kinase-Activated Protein Kinase, Isolated by a Novel Expression Screening Method for Identifying Protein Kinase Substrates", The EMBO Journal, 16(8):1921-1933.
Hou et al. (Feb. 2012) "Targeting Mnks for Cancer Therapy", Oncotarget, 3(2):118-131.
Huang et al. (May 30, 2020) "The MNK1/2-eIF4E Axis Drives Melanoma Plasticity, Progression, and Resistance to Immunotherapy", bioRxiv, 1-57.
Khabar Khalid S.A. (Jan. 11, 2005) "The AU-Rich Transcriptome: More Than Interferons and Cytokines, and Its Role in Disease", Journal of Interferon & Cytokine Research, 25:1-10.
Konicek et al. (Mar. 1, 2011) "Therapeutic Inhibition of MAP Kinase Interacting Kinase Blocks Eukaryotic Initiation Factor 4E Phosphorylation and Suppresses Outgrowth of Experimental Lung Metastases", Cancer Research, 71(5):1849-1857.
Li et al. (Jul. 23, 2016) "Inhibition of Mnk Enhances Apoptotic Activity of Cytarabine in Acute Myeloid Leukemia Cells", Oncotarget, 7(35):56811-56825.
Nikolcheva et al. (2002) "A Translational Rheostat for RFLAT-1 Regulates RANTES Expression in T Lymphocytes", The Journal of Clinical Investigation, 110(1):119-126.
Oyarzabal et al. (Sep. 23, 2010) "Discovery of Mitogen-Activated Protein Kinase-Interacting Kinase 1 Inhibitors by a Comprehensive Fragment-Oriented Virtual Screening Approach", Journal of Medicinal Chemistry, 53(18):6618-6628.
Pubmed (Feb. 23, 2016) "Tomivosertib", United State National Library of Medicine, Available at: https://pubchem.ncbi.nlm.nih.gov/compound/118598754, 26 pages.
Reich et al. (Apr. 26, 2018) "Structure-based Design of Pyridone-Aminal eFT508 Targeting Dysregulated Translation by Selective Mitogen-activated Protein Kinase Interacting Kinases 1 and 2 (MNK1/2) Inhibition", Journal of Medicinal Chemistry, 61(8):3516-3540.
Rowlett et al. (Nov. 21, 2007) "MNK Kinases Regulate Multiple TLR Pathways and Innate Proinflammatory Cytokines in Macrophages", American Journal of Physiology-Gastrointestinal and Liver Physiology, 294(2):G452-G459.
Teo et al. (2015) "An Integrated Approach for Discovery Of Highly Potent And Selective Mnk Inhibitors: Screening, Synthesis And SAR Analysis", European Journal of Medicinal Chemistry, 103:539-550.
Ueda et al. (2004) "Mnk2 and Mnk1 Are Essential for Constitutive and Inducible Phosphorylation of Eukaryotic Initiation Factor 4E but Not for Cell Growth or Development", Molecular and Cellular Biology, 24(15):6539-6549.
Venkatesh et al. (Feb. 2000) "Role Of The Development Scientist In Compound Lead Selection And Optimization", Journal of Pharmaceutical Sciences, 89(2):145-154.
Wiedemann et al. (2009) ". . . and honour their art!—Evaluation of Historical and New Routes to 1,5-Dihydroxy-6-oxo-1,6-dihydropyridine- (56) References Cited

OTHER PUBLICATIONS 2-carboxylicAcid and 1,3-Dihydroxy-2-oxo-3-pyrroline-4-carboxylicAcid", A Journal of Chemical Sciences, 64b:1276-1288.
Xu et al. (Jan. 14, 2019) "Translation Control of the Immune Checkpoint in Cancer and its Therapeutic Targeting", Nature Medicine, 25(2):301-311.
Yu et al. (May 5, 2015) "Discovery of 4-(Dihydropyridinon-3-Yl) Amino-5-Methylthieno[2,3-D]Pyrimidine Derivatives as Potent Mnk Inhibitors: Synthesis, Structure-Activity Relationship Analysis and Biological Evaluation", European Journal of Medicinal Chemistry, 95:116-126.
Caira, Mino R. (1998) "Crystalline Polymorphism of Organic Compounds", Topics in Current Chemistry, 198:163-208.
Kümmerer, Klaus (Nov. 2010) "Pharmaceuticals in the Environment", Annual Review of Environment and Resources, , 35:57-75.
Morissette et al. (2004) "High-throughput Crystallization: Polymorphs, Salts, Co-crystals and Solvates of Pharmaceutical Solids", Advance Drug Delivery Reviews, 56(3):275-300.
Variankaval et al. (2008) "From Form to Function: Crystallization of Active Pharmaceutical Ingredients", Aiche Journal, 54(7):1682-1688.

CRYSTALLINE FORMS OF MNK INHIBITORS

CROSS-REFERENCE OF RELATED APPLICATIONS

This application is a continuation of U.S. patent application Ser. No. 16/661,507, filed Oct. 23, 2019, which claims the benefit of U.S. Provisional Application No. 62/749,820, filed Oct. 24, 2018, each of which is herein incorporated by reference.

FIELD

The present invention generally relates to crystalline forms of a compound having activity as an inhibitor of MAP kinase-interacting kinase (Mnk), for example Mnk1 and Mnk2, as well as to pharmaceutical compositions and processes for making the inventive compound, which is utilized as a therapeutic agent for the treatment of Mnk dependent diseases, including the treatment of cancer.

BACKGROUND

Eukaryotic initiation factor 4E (eIF4E) is a general translation factor but it has the potential to enhance preferentially the translation of messenger RNAs (mRNAs) that lead to the production of malignancy-associated proteins. This selectivity may relate to an increased requirement for eIF4E and its binding partners for the translation of mRNAs containing extensive secondary structure in their 5'-untranslated regions (5'-UTRs). Elevated levels of eIF4E have been found in many types of tumors and cancer cell lines including cancers of the colon, breast, bladder, lung, prostate, gastrointestinal tract, head and neck, Hodgkin's lymphomas and neuroblastomas.

The PI3K (phosphoinositide 3-kinase)/PTEN (phosphatase and tensin homologue deleted on chromosome ten)/Akt/mTOR (mammalian target of rapamycin) pathway is important in regulating mRNA translation of genes that encode for pro-oncogenic proteins and activated mTORC1 signaling in a high proportion of cancers, these kinases have been actively pursued as oncology drug targets. A number of pharmacological inhibitors have been identified, some of which have reached advanced clinical stages. However, it has recently become clear that the mTOR pathway participates in a complicated feedback loop that can impair activation of Akt.

Mnk1 and Mnk2 are threonine/serine protein kinases and specifically phosphorylate serine 209 (Ser209) of eIF4E within the eIF4F complex. While Mnk activity is necessary for eIF4E-mediated oncogenic transformation, it is dispensable for normal development. Pharmacologically inhibiting Mnks thus presents an attractive therapeutic strategy for cancer.

Despite increased understanding of Mnk structure and function, little progress has been made with regard to the discovery of pharmacological Mnk inhibitors and relatively few Mnk inhibitors have been reported: CGP052088 (Tschopp et al., *Mol Cell Biol Res Commun.* 3(4):205-211, 2000); CGP57380 (Rowlett et al., *Am J Physiol Gastrointest Liver Physiol.* 294(2):G452-459, 2008); and Cercosporamide (Konicek et al., *Cancer Res.* 71(5):1849-1857, 2011). These compounds, however, have mainly been used for the purpose of Mnk target validation. More recently, investigators have proposed further compounds for treating diseases influenced by the inhibition of kinase activity of Mnk1 and/or Mnk2, including, for example, the compounds disclosed in International Patent Application no. WO/2017/075394; U.S. Pat. Nos. 9,382,248; 9,669,031; and 9,814,718.

Accordingly, while advances have been made in this field there remains a significant need in the art for compounds and pharmaceutically acceptable compositions that effectively inhibit Mnk kinase activity, particularly with regard to Mnk's role in the regulation of cancer pathways, as well as for associated composition and methods. The present invention fulfills this need and provides further related advantages.

SUMMARY

The present invention is directed to crystalline forms of a compound that inhibit or modulate the activity of Mnk. The present invention also is directed to pharmaceutically acceptable compositions containing such a compound and associated methods for treating conditions that would benefit from Mnk inhibition, such as cancer.

In one embodiment the invention is directed to a crystalline compound of:

or stereoisomers, tautomers, or solvates thereof.

In another embodiment, the invention is directed to a crystalline compound wherein the compound has an X-ray powder diffraction pattern with characteristic peaks expressed in values of degrees 2Θ at about 8.07; about 10.81; about 14.68; and about 22.07±0.2.

In an embodiment, the crystalline solid of the compound has an X-ray powder diffraction pattern with characteristic peaks expressed in values of degrees 2Θ at about 8.07; about 10.81; about 14.68; about 16.69; about 17.34; and about 22.07±0.2.

In another embodiment, the crystalline solid of the compound has an X-ray powder diffraction pattern with characteristic peaks expressed in values of degrees 2Θ at about 8.07; about 10.81; about 12.00; about 12.37; about 13.79; about 14.68; about 15.39; about 16.19; about 16.69; about 17.34; about 18.89; about 20.26; about 21.15; about 21.30; about 21.77; about 22.07; about 22.84; about 23.49; about 24.40; about 24.90; about 25.34; about 25.75; about 26.12; about 26.54; about 27.16; about 27.48; about 28.06; about 28.76; about 29.04; about 29.26; and about 29.59±0.2.

Figure 1:
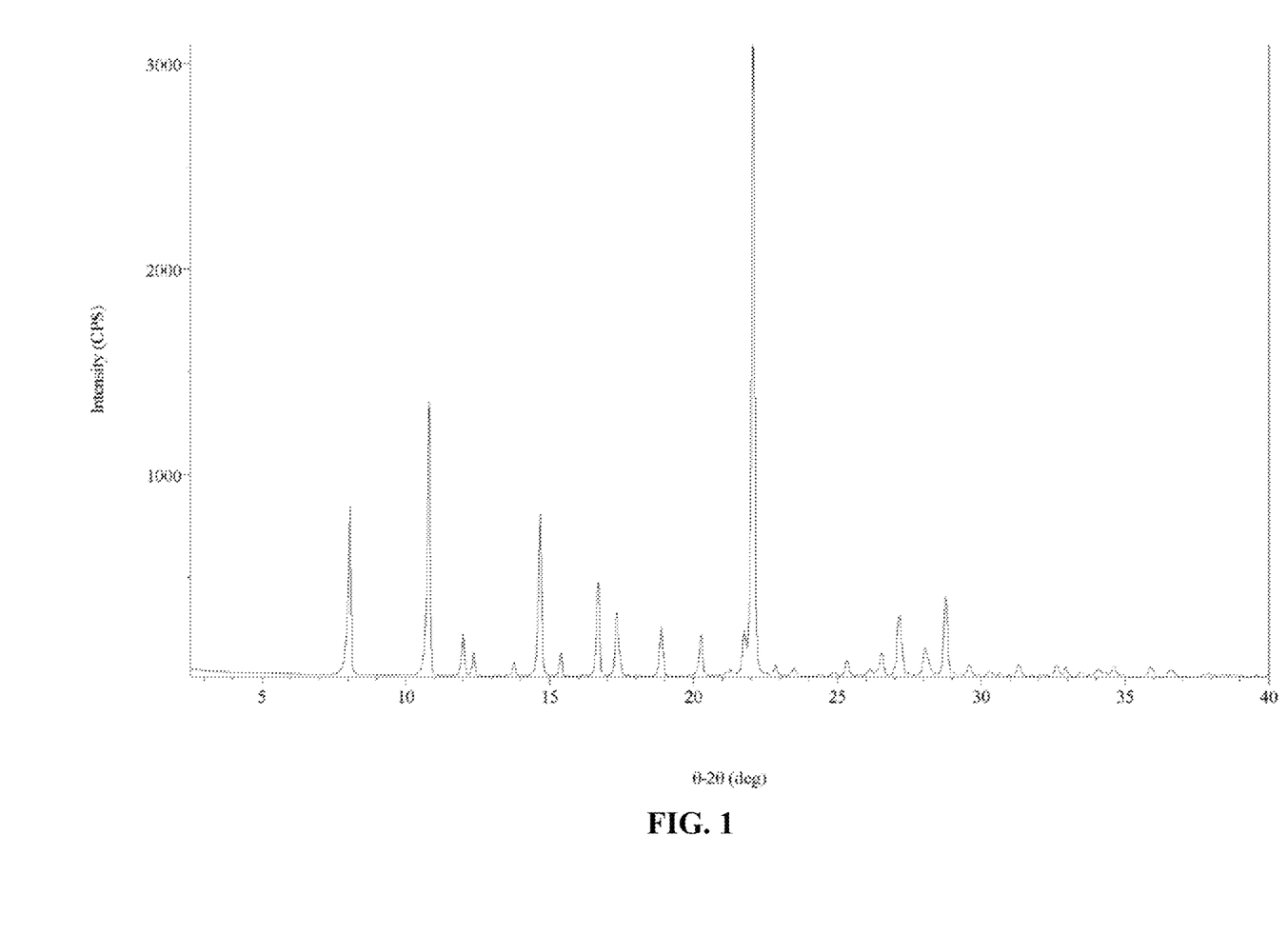
FIG. 1 shows the XRPD pattern of Form A of 6'-((6-aminopyrimidin-4-yl)amino)-8'-methyl-2'H-spiro[cyclohexane-1,3'-imidazo[1,5-a]pyridine]-1',5'-dione.

In a further embodiment, the crystalline solid has an X-ray powder diffraction pattern substantially as shown in FIG. 1.

The present invention also provides a pharmaceutical composition comprising (i) a therapeutically effective amount of at least one crystalline solid according to the present application or a stereoisomer, tautomer, or solvate thereof; (ii) in combination with a pharmaceutically acceptable carrier, diluent or excipient.

Also provided by the present invention is a method for attenuating or inhibiting the activity of Mnk in at least one cell overexpressing Mnk, comprising contacting the at least one cell with a compound according to the present application or a stereoisomer, tautomer, or solvate thereof.

According to the inventive method at least one cell is a colon cancer cell, a gastric cancer cell, a thyroid cancer cell, a lung cancer cell, a leukemia cell, a B-cell lymphoma, a T-cell lymphoma, a hairy cell lymphoma, Hodgkin's lymphoma cell, non-Hodgkin's lymphoma cell, Burkitt's lymphoma cell, a pancreatic cancer cell, a melanoma cell, a multiple melanoma cell, a brain cancer cell, a CNS cancer cell, a renal cancer cell, a prostate cancer cell, an ovarian cancer cell, or a breast cancer cell.

The present invention provides a method for treating an Mnk dependent condition in a mammal in need thereof, comprising administering to the mammal (i) a therapeutically effective amount of at least one compound according to the present application or a stereoisomer, tautomer, or solvate thereof, or (ii) a pharmaceutical composition the a compound of the present application.

In an embodiment, the condition treated by the inventive method is colorectal cancer, gastric cancer, thyroid cancer, lung cancer, leukemia, B-cell lymphoma, T-cell lymphoma, hairy cell lymphoma, Hodgkin's lymphoma, non-Hodgkin's lymphoma, Burkitt's lymphoma, pancreatic cancer, melanoma, multiple melanoma, brain cancer, CNS cancer, renal cancer, prostate cancer, ovarian cancer or breast cancer. In another embodiment, the mammal of the inventive method is a human.

The above embodiments and other aspects of the invention are readily apparent in the detailed description that follows. To this end, various references are set forth herein which describe in more detail certain background information, procedures, compounds and/or compositions, and are each hereby incorporated by reference in their entirety.

DETAILED DESCRIPTION

In the following description, certain specific details are set forth in order to provide a thorough understanding of various embodiments of the invention. However, one skilled in the art will understand that the invention may be practiced without these details. Unless the context requires otherwise, throughout the present specification and claims, the word "comprise" and variations thereof, such as, "comprises" and "comprising" are to be construed in an open, inclusive sense (i.e., as "including, but not limited to").

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Definitions

As used herein, and unless noted to the contrary, the following terms and phrases have the meaning noted below.

The compound of the invention can exist in various isomeric forms, as well as in one or more tautomeric forms, including both single tautomers and mixtures of tautomers. The term "isomer" is intended to encompass all isomeric forms of a compound of this invention, including tautomeric forms of the compound.

Some compounds described here can have asymmetric centers and therefore exist in different enantiomeric and diastereomeric forms. A compound of the invention can be in the form of an optical isomer or a diastereomer. Accordingly, the invention encompasses compounds of the invention and their uses as described herein in the form of their optical isomers, diastereoisomers and mixtures thereof, including a racemic mixture. Optical isomers of the compounds of the invention can be obtained by known techniques such as asymmetric synthesis, chiral chromatography, or via chemical separation of stereoisomers through the employment of optically active resolving agents.

Unless otherwise indicated, "stereoisomer" means one stereoisomer of a compound that is substantially free of other stereoisomers of that compound. Thus, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, for example greater than about 90% by weight of one stereoisomer of the compound and less than about 10% by weight of the other stereoisomers of the compound, or greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound.

If there is a discrepancy between a depicted structure and a name given to that structure, then the depicted structure controls. Additionally, if the stereochemistry of a structure or a portion of a structure is not indicated with, for example, bold or dashed lines, the structure or portion of the structure is to be interpreted as encompassing all stereoisomers of it. In some cases, however, where more than one chiral center exists, the structures and names may be represented as single enantiomers to help describe the relative stereochemistry. Those skilled in the art of organic synthesis will know if the compounds are prepared as single enantiomers from the methods used to prepare them.

The terms "treat," "treating" and "treatment" refer to the amelioration or eradication of a disease or symptoms associated with a disease. In certain embodiments, such terms refer to minimizing the spread or worsening of the disease resulting from the administration of one or more prophylactic or therapeutic agents to a patient with such a disease. In the context of the present invention the terms "treat," "treating" and "treatment" also refer to:

(i) preventing the disease or condition from occurring in a mammal, in particular, when such mammal is predisposed to the condition but has not yet been diagnosed as having it;

(ii) inhibiting the disease or condition, i.e., arresting its development;

(iii) relieving the disease or condition, i.e., causing regression of the disease or condition; or (iv) relieving the symptoms resulting from the disease or condition, i.e., relieving pain without addressing the underlying disease or condition. As used herein, the terms "disease" and "condition" may be used interchangeably or may be different in that the particular malady or condition may not have a known causative agent (or that the etiology has not yet been worked out) and it is therefore not yet recognized as a disease but only as an undesirable condition or syndrome, wherein a more or less specific set of symptoms have been identified by clinicians.

The terms "modulate," "modulation" and the like refer to the ability of a compound to increase or decrease the function, or activity of, for example, MAP kinase interacting kinase (Mnk). "Modulation," in its various forms, is intended to encompass inhibition, antagonism, partial antagonism, activation, agonism and/or partial agonism of the activity associated with Mnk. Mnk inhibitors are compounds that bind to, partially or totally block stimulation, decrease, prevent, delay activation, inactivate, desensitize, or down regulate signal transduction. The ability of a compound to modulate Mnk activity can be demonstrated in an enzymatic assay or a cell-based assay.

A "patient" or "subject" includes an animal, such as a human, cow, horse, sheep, lamb, pig, chicken, turkey, quail, cat, dog, mouse, rat, rabbit or guinea pig. The animal can be a mammal such as a non-primate and a primate (e.g., monkey and human). In one embodiment, a patient is a human, such as a human infant, child, adolescent or adult.

The term "prodrug" refers to a precursor of a drug, a compound which upon administration to a patient, must undergo chemical conversion by metabolic processes before becoming an active pharmacological agent. Exemplary prodrugs of compounds of the present application are esters, acetamides, and amides.

The inventive compounds may be isotopically-labelled by having one or more atoms replaced by an atom having a different atomic mass or mass number. Examples of isotopes that can be incorporated include isotopes of hydrogen, carbon, nitrogen, oxygen, phosphorous, fluorine, chlorine, or iodine. Illustrative of such isotopes are $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{36}$Cl, $^{123}$I, and $^{125}$I, respectively. These radiolabelled compounds can be used to measure the biodistribution, tissue concentration and the kinetics of transport and excretion from biological tissues including a subject to which such a labelled compound is administered. Labeled compounds are also used to determine therapeutic effectiveness, the site or mode of action, and the binding affinity of a candidate therapeutic to a pharmacologically important target. Certain radioactive-labelled compounds are useful in drug and/or tissue distribution studies. The radioactive isotopes tritium, i.e., $^3$H and carbon-14, i.e., $^{14}$C, are particularly useful for this purpose in view of their ease of incorporation and means of detection.

Substitution with heavier isotopes such as deuterium, i.e., $^2$H, affords certain therapeutic advantages resulting from the greater metabolic stability, for example, increased in vivo half-life of compounds containing deuterium. Substitution of hydrogen with deuterium may reduce dose required for therapeutic effect, and hence may be preferred in a discovery or clinical setting.

Substitution with positron emitting isotopes, such as $^{11}$C, $^{18}$F, $^{15}$O and $^{13}$N, provides labeled analogs of the inventive compounds that are useful in Positron Emission Tomography (PET) studies, e.g., for examining substrate receptor occupancy. Isotopically-labeled compounds according to the present application can generally be prepared by conventional techniques known to those skilled in the art or by processes analogous to those described in the Example section as set out below using an appropriate isotopic-labeling reagent.

Embodiments of the invention disclosed herein are also meant to encompass the in vivo metabolic products of compounds of the present application. Such products may result from, for example, the oxidation, reduction, hydrolysis, amidation, esterification, and like processes primarily due to enzymatic activity upon administration of a compound of the invention. Accordingly, the invention includes compounds that are produced as by-products of enzymatic or non-enzymatic activity on an inventive compound following the administration of such a compound to a mammal for a period of time sufficient to yield a metabolic product. Metabolic products, particularly pharmaceutically active metabolites, are typically identified by administering a radiolabelled compound of the invention in a detectable dose to a subject, such as rat, mouse, guinea pig, monkey, or human, for a sufficient period of time during which metabolism occurs, and isolating the metabolic products from urine, blood or other biological samples that are obtained from the subject receiving the radiolabelled compound.

Often crystallizations produce a solvate of the compound of the invention. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compound of the invention may be true solvates, while in other cases, the compound of the invention may merely retain adventitious water or be a mixture of water plus some adventitious solvent.

Compounds of the invention, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included.

The term "tautomer" refers to a proton shift from one atom of a molecule to another atom of the same molecule.

The inventive compounds are synthesized using conventional synthetic methods, and more specifically using the general methods noted below. Specific synthetic protocols for compounds in accordance with the present invention are described in the Examples.

Pharmaceutical Formulations

In one embodiment, compounds of the present application are formulated as pharmaceutically acceptable compositions that contain the compound in an amount effective to treat a particular disease or condition of interest upon administration of the pharmaceutical composition to a mammal. Pharmaceutical compositions in accordance with the present invention can comprise a compound in combination with a pharmaceutically acceptable carrier, diluent or excipient.

In this regard, a "pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

Further, a "mammal" includes humans and both domestic animals such as laboratory animals and household pets (e.g., cats, dogs, swine, cattle, sheep, goats, horses, rabbits), and non-domestic animals such as wildlife and the like.

The pharmaceutical compositions of the invention can be prepared by combining a compound of the invention with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Typical routes of administering such pharmaceutical compositions include, without limitation, oral, topical, transdermal, inhalation, parenteral, sublingual, buccal, rectal, vaginal, and intranasal. The term parenteral as used herein includes subcutaneous injections, intravenous, intramuscular, intrastemal injection or infusion techniques. Pharmaceutical compositions of the invention are formulated so as to allow the active ingredients contained therein to be bioavailable upon administration of the composition to a patient. Compositions that will be administered to a subject or patient take the form of one or more dosage units, where for example, a tablet may be a single dosage unit, and a container of a compound of the invention in aerosol form may hold a plurality of dosage units. Actual methods of preparing such dosage forms are known, or will be apparent, to those skilled in this art; for example, see Remington: The Science and Practice of Pharmacy, 20th Edition (Philadelphia College of Pharmacy and Science, 2000). The composition to be administered will, in any event, contain a therapeutically effective amount of a compound of the invention, or a pharmaceutically acceptable salt thereof, for treatment of a disease or condition of interest in accordance with the teachings of this invention.

A pharmaceutical composition of the invention may be in the form of a solid or liquid. In one aspect, the carrier(s) are particulate, so that the compositions are, for example, in tablet or powder form. The carrier(s) may be liquid, with the compositions being, for example, an oral syrup, injectable liquid or an aerosol, which is useful in, for example, inhalatory administration. When intended for oral administration, the pharmaceutical composition is preferably in either solid or liquid form, where semi-solid, semi-liquid, suspension and gel forms are included within the forms considered herein as either solid or liquid.

As a solid composition for oral administration the pharmaceutical composition may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, for example, a gelatin capsule, it may contain, in addition to materials of the above type, a liquid carrier such as polyethylene glycol or oil.

The pharmaceutical composition may be in the form of a liquid, for example, an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition of the invention intended for either parenteral or oral administration should contain an amount of a compound of the invention such that a suitable dosage will be obtained.

The pharmaceutical composition of the invention may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device.

The pharmaceutical composition of the invention may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition of the invention may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

The pharmaceutical composition of the invention in solid or liquid form may include an agent that binds to the compound of the invention and thereby assists in the delivery of the compound. Suitable agents that may act in this capacity include a monoclonal or polyclonal antibody, a protein or a liposome.

The pharmaceutical composition of the invention may consist of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of the invention may be delivered in single phase, bi-phasic, or tri-phasic systems in order to deliver the active ingredient(s). Delivery of the aerosol includes the necessary container, activators, valves, subcontainers, and the like, which together may form a kit. One skilled in the art, without undue experimentation may determine preferred aerosols.

The pharmaceutical compositions of the invention may be prepared by any methodology well known in the pharmaceutical art. For example, a pharmaceutical composition intended to be administered by injection can be prepared by combining a compound of the invention with sterile, distilled water so as to form a solution. A surfactant may be added to facilitate the formation of a homogeneous solution or suspension. Surfactants are compounds that non-covalently interact with the compound of the invention so as to facilitate dissolution or homogeneous suspension of the compound in the aqueous delivery system.

In certain embodiments a pharmaceutical composition comprising a compound of the present application is administered to a mammal in an amount sufficient to inhibit Mnk activity upon administration, and preferably with acceptable toxicity to the same. Mnk activity of the crystalline form of the compounds of the present application can be determined by one skilled in the art, for example, as described in the Examples below. Appropriate concentrations and dosages can be readily determined by one skilled in the art.

In a further aspect of the invention the inventive compounds or pharmaceutically acceptable formulations of the inventive compounds are provided as inhibitors of Mnk activity. Such inhibition is achieved by contacting a cell expressing Mnk with a compound or a pharmaceutically acceptable formulation, to lower or inhibit Mnk activity, to provide therapeutic efficacy for a Mnk dependent condition in a mammal in need thereof.

Therapeutically effective dosages of a compound according to the present application or a pharmaceutical composition of the present application will generally range from about 1 to 2000 mg/day, from about 10 to about 1000 mg/day, from about 10 to about 500 mg/day, from about 10 to about 250 mg/day, from about 10 to about 100 mg/day, or from about 10 to about 50 mg/day. The therapeutically effective dosages may be administered in one or multiple doses. It will be appreciated, however, that specific doses of the compounds of the invention for any particular patient will depend on a variety of factors such as age, sex, body weight, general health condition, diet, individual response of the patient to be treated, time of administration, severity of the disease to be treated, the activity of particular compound applied, dosage form, mode of application and concomitant medication. The therapeutically effective amount for a given situation will readily be determined by routine experimentation and is within the skills and judgment of the ordinary clinician or physician. In any case, the compound or composition will be administered at dosages in a manner which allows a therapeutically effective amount to be delivered based upon patient's unique condition.

A dosage form as presently described can also preferably include a disintegrant, which functions to cause the dosage form to expand and break up during use, e.g., at conditions of a human stomach, to allow active pharmaceutical ingredient of the dosage form to be released in a manner to achieve an immediate release profile. Disintegrants are ingredients of pharmaceutical dosage forms, with various examples being known and commercially available. Examples of disintegrants include compositions of or containing citric acid, sodium bicarbonate, or any combination of two or more of the foregoing, and other pharmaceutically acceptable materials formed into particles having a particle size, density, etc., to allow processing of the disintegrant into a useful immediate release dosage form.

The disintegrant can be present in an immediate release dosage form at any location that allows the disintegrant to function as desired, to expand within the intact dosage form, upon ingestion, to cause the ingested dosage form to break apart and allow for desired immediate release of active pharmaceutical ingredient from the dosage form, in a stomach. One useful location for a disintegrant can be as a component of an excipient used to contain core-shell particles that contain active pharmaceutical ingredient, as described herein, in a dosage form such as a compressed tablet or capsule.

When included as an excipient of a dosage form, disintegrant may be present in an amount useful to achieve immediate release of an API of a dosage form. Examples of useful amounts of disintegrant in an immediate release dosage form as described herein may be in a range from 0.5 to 50 weight percent disintegrant based on a total weight of the dosage form, e.g., from 1 to 30 weight percent disintegrant based on total weight of the dosage form. The amount of disintegrant in a matrix of a dosage form can be consistent with these amounts, e.g., disintegrant can be included in a matrix (e.g., total of a dosage form that is other than the coated particles or API) of a dosage form in an amount in a range from 0.5 to 50 weight percent disintegrant based on a total weight of the matrix, e.g., from 1 to 30 weight percent disintegrant based on total weight matrix.

A dosage form as described can also include any of various known and conventional pharmaceutical excipients that may be useful to achieve desired processing and performance properties of an immediate release dosage form. These excipients include fillers, binders, lubricants, glidants, etc., and can be included in core-shell particles or in a matrix (e.g., compressed matrix) of a tablet or capsule. A more detailed description of pharmaceutical excipients that may also be included in the tablets of the present invention can be found in The Handbook of Pharmaceutical Excipients, 5th ed. (2006).

Examples of fillers that may be useful in an immediate release dosage form as described include lactose, starch, dextrose, sucrose, fructose, maltose, mannitol, sorbitol, kaolin, microcrystalline cellulose, powdered cellulose, calcium sulfate, calcium phosphate, dicalcium phosphate, lactitol or any combination of the foregoing.

A filler may be present in any portion of a dosage form as described, including a core-shell particle; the filler may be present in a core, in a layer containing an active pharmaceutical ingredient that is disposed on the core, in a solvent resistant film, in the matrix, or in two or more of these portions of the dosage form. The filler may be present at any one or more of these portions of a dosage form in an amount to provide desired processing or functional properties of a portion of the dosage form and of the entire dosage form. The amount of total filler in a dosage form can also be as desired to provide desired functionality, including an immediate release profile, for example in an amount in a range from 0 to 80 weight percent filler based upon the total weight of the dosage form, e.g. from 5 to 50 percent filler based on total weight dosage form.

Examples of lubricants include inorganic materials such as talc (a hydrated magnesium silicate; polymers, such as, PEG 4000; fatty acids, such as stearic acid; fatty acid esters, such as glyceride esters (e.g., glyceryl monostearate, glyceryl tribehenate, and glyceryl dibehenate); sugar esters (e.g., sorbitan monostearate and sucrose monopalmitate); glyceryl dibehenate; and metal salts of fatty acids (e.g., sodium lauryl sulfate, magnesium stearate, calcium stearate, and zinc stearate). Lubricant may be included in an immediate release dosage form, in any useful amount, such as an amount in a range from 0.1 to 10 weight percent lubricant based on a total weight of a dosage form, e.g., from 0.5 to 7 weight percent lubricant based on total weight dosage form.

Examples of glidants include colloidal silicon dioxide, untreated fumed silica (AEROSOL 200@), and crystalline or fused quartz. Glidant may be included in an immediate release dosage form as described, in any useful amount.

Therapeutic Use

The compounds of the invention, or their pharmaceutically acceptable salts, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy.

"Effective amount" or "therapeutically effective amount" refers to that amount of a compound of the invention which, when administered to a mammal, preferably a human, is sufficient to effect treatment, as defined below, of a Mnk related condition or disease in the mammal, preferably a human. The amount of a compound of the invention which constitutes a "therapeutically effective amount" will vary depending on the compound, the condition and its severity, the manner of administration, and the age of the mammal to be treated, but can be determined routinely by one of ordinary skill in the art having regard to his own knowledge and to this disclosure.

Compounds of the invention, or pharmaceutically acceptable salt thereof, may also be administered simultaneously with, prior to, or after administration of one or more other therapeutic agents. Such combination therapy includes administration of a single pharmaceutical dosage formulation which contains a compound of the invention and one or more additional active agents, as well as administration of the compound of the invention and each active agent in its own separate pharmaceutical dosage formulation. For example, a compound of the invention and the other active agent can be administered to the patient together in a single oral dosage composition such as a tablet or capsule, or each agent administered in separate oral dosage formulations. Where separate dosage formulations are used, the compounds of the invention and one or more additional active agents can be administered at essentially the same time, i.e., concurrently, or at separately staggered times, i.e., sequentially; combination therapy is understood to include all these regimens.

In certain embodiments the disclosed compounds are useful for inhibiting the activity of Mnk and/or can be useful in analyzing Mnk signaling activity in model systems and/or for preventing, treating, or ameliorating a symptom associated with a disease, disorder, or pathological condition involving Mnk, preferably one afflicting humans. A compound which inhibits the activity of Mnk will be useful in preventing, treating, ameliorating, or reducing the symptoms or progression of diseases of uncontrolled cell growth, proliferation and/or survival, inappropriate cellular immune responses, or inappropriate cellular inflammatory responses or diseases which are accompanied with uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by Mnk, such as, for example, haematological tumors, solid tumors, and/or metastases thereof, including leukaemias and myelodysplastic syndrome, Waldenstrom macroglobulinemia, and malignant lymphomas, for example, B-cell lymphoma, T-cell lymphoma, hairy cell lymphoma, Hodgkin's lymphoma, non-Hodgkin's lymphoma, and Burkitt's lymphoma, head and neck tumors including brain tumors and brain metastases, tumors of the thorax including non-small cell and small cell lung tumors, gastrointestinal tumors, endocrine tumors, mammary and other gynecological tumors, urological tumors including renal, bladder and prostate tumors, skin tumors, and sarcomas, and/or metastases thereof.

Furthermore, the inventive compounds and their pharmaceutical compositions are candidate therapeutics for the prophylaxis and/or therapy of cytokine related diseases, such as inflammatory diseases, allergies, or other conditions associated with proinflammatory cytokines. Exemplary inflammatory diseases include without limitation, chronic or acute inflammation, inflammation of the joints such as chronic inflammatory arthritis, rheumatoid arthritis, psoriatic arthritis, osteoarthritis, juvenile rheumatoid arthritis, Reiter's syndrome, rheumatoid traumatic arthritis, rubella arthritis, acute synovitis and gouty arthritis; inflammatory skin diseases such as sunburn, psoriasis, erythrodermic psoriasis, pustular psoriasis, eczema, dermatitis, acute or chronic graft formation, atopic dermatitis, contact dermatitis, urticaria and scleroderma; inflammation of the gastrointestinal tract such as inflammatory bowel disease, Crohn's disease and related conditions, ulcerative colitis, colitis, and diverticulitis; nephritis, urethritis, salpingitis, oophoritis, endomyometritis, spondylitis, systemic lupus erythematosus and related disorders, multiple sclerosis, asthma, meningitis, myelitis, encephalomyelitis, encephalitis, phlebitis, thrombophlebitis, respiratory diseases such as asthma, bronchitis, chronic obstructive pulmonary disease (COPD), inflammatory lung disease and adult respiratory distress syndrome, and allergic rhinitis; endocarditis, osteomyelitis, rheumatic fever, rheumatic pericarditis, rheumatic endocarditis, rheumatic myocarditis, rheumatic mitral valve disease, rheumatic aortic valve disease, prostatitis, prostatocystitis, spondoarthropathies ankylosing spondylitis, synovitis, tenosynovotis, myositis, pharyngitis, polymyalgia rheumatica, shoulder tendonitis or bursitis, gout, pseudo gout, vasculitides, inflammatory diseases of the thyroid selected from granulomatous thyroiditis, lymphocytic thyroiditis, invasive fibrous thyroiditis, acute thyroiditis; Hashimoto's thyroiditis, Kawasaki's disease, Raynaud's phenomenon, Sjogren's syndrome, neuroinflammatory disease, sepsis, conjunctivitis, keratitis, iridocyclitis, optic neuritis, otitis, lymphoadenitis, nasopaharingitis, sinusitis, pharyngitis, tonsillitis, laryngitis, epiglottitis, bronchitis, pneumonitis, stomatitis, gingivitis, oesophagitis, gastritis, peritonitis, hepatitis, cholelithiasis, cholecystitis, glomerulonephritis, goodpasture's disease, crescentic glomerulonephritis, pancreatitis, endomyometritis, myometritis, metritis, cervicitis, endocervicitis, exocervicitis, parametritis, tuberculosis, vaginitis, vulvitis, silicosis, sarcoidosis, pneumoconiosis, pyresis, inflammatory polyarthropathies, psoriatric arthropathies, intestinal fibrosis, bronchiectasis and enteropathic arthropathies.

Accordingly, certain embodiments are directed to a method for treating a Mnk dependent condition in a mammal in need thereof, the method comprising administering an effective amount of a pharmaceutical composition as described above (i.e., a pharmaceutical composition comprising any one or more compounds of the present application to a mammal.

As described above deregulation of protein synthesis is a common event in human cancers. A key regulator of translational control is eIF4E whose activity is a key determinant of tumorigenicity. Because activation of eIF4E involves phosphorylation of a key serine (Ser209) specifically by MAP kinase interacting kinases (Mnk), inhibitors of Mnk are suitable candidate therapeutics for treating cell proliferative disorders such as cancer. A wide variety of cancers, including solid tumors, lymphomas and leukemias, are amenable to the compositions and methods disclosed herein. Types of cancer that may be treated include, but are not limited to: adenocarcinoma of the breast, prostate and colon; all forms of bronchogenic carcinoma of the lung; myeloid; melanoma; hepatoma; neuroblastoma; papilloma; apudoma; choristoma; branchioma; malignant carcinoid syndrome; carcinoid heart disease; and carcinoma (e.g., Walker, basal cell, basosquamous, Brown-Pearce, ductal, Ehrlich tumor, Krebs 2, merkel cell, mucinous, non-small cell lung, oat cell, papillary, scirrhous, bronchiolar, bronchogenic, squamous cell, and transitional cell). Additional types of cancers that may be treated include: histiocytic disorders; acute and chronic leukemia, both myeloid and lymphoid/lymphoblastic, including hairy cell leukemia; histiocytosis malignant; Hodgkin's disease; immunoproliferative small; Hodgkin's lymphoma; B-cell and T-cell non-Hodgkin's lymphoma, including diffuse large B-cell and Burkitt's lymphoma; plasmacytoma; reticuloendotheliosis; melanoma; multiple myeloma; chondroblastoma; chondroma; chondrosarcoma; fibroma; fibrosarcoma; myelofibrosis; giant cell tumors; histiocytoma; lipoma; liposarcoma; mesothelioma; myxoma; myxosarcoma; osteoma; osteosarcoma; chordoma; craniopharyngioma; dysgerminoma; hamartoma; mesenchymoma; mesonephroma; myosarcoma; ameloblastoma; cementoma; odontoma; teratoma; thymoma; trophoblastic tumor.

Other cancers that can be treated using the inventive compounds include without limitation adenoma; cholangioma; cholesteatoma; cyclindroma; cystadenocarcinoma; cystadenoma; granulosa cell tumor; gynandroblastoma; hepatoma; hidradenoma; islet cell tumor; Leydig cell tumor; papilloma; sertoli cell tumor; theca cell tumor; leimyoma; leiomyosarcoma; myoblastoma; myomma; myosarcoma; rhabdomyoma; rhabdomyosarcoma; ependymoma; ganglioneuroma; glioma; medulloblastoma; meningioma; neurilemmoma; neuroblastoma; neuroepithelioma; neurofibroma; neuroma; paraganglioma; paraganglioma nonchromaffin.

In one embodiment the inventive compounds are candidate therapeutic agents for the treatment of cancers such as angiokeratoma; angiolymphoid hyperplasia with eosinophilia; angioma sclerosing; angiomatosis; glomangioma; hemangioendothelioma; hemangioma; hemangiopericytoma; hemangiosarcoma; lymphangioma; lymphangiomyoma; lymphangiosarcoma; pinealoma; carcinosarcoma; chondrosarcoma; cystosarcoma phyllodes; fibrosarcoma; hemangiosarcoma; leiomyosarcoma; leukosarcoma; liposarcoma; lymphangiosarcoma; myosarcoma; myxosarcoma; ovarian carcinoma; rhabdomyosarcoma; sarcoma; neoplasms; nerofibromatosis; and cervical dysplasia.

In a particular embodiment the present disclosure provides methods for treating colon cancer, colorectal cancer, gastric cancer, thyroid cancer, lung cancer, leukemia, pancreatic cancer, melanoma, multiple melanoma, brain cancer, primary and secondary CNS cancer, including malignant glioma and glioblastoma, renal cancer, prostate cancer, including castration-resistant prostate cancer, ovarian cancer, or breast cancer, including triple negative, HER2 positive, and hormone receptor positive breast cancers. According to such a method, a therapeutically effective amount of at least one compound of the present application or a stereoisomer, tautomer, or solvate thereof can be administered to a subject who has been diagnosed with a cell proliferative disease, such as a cancer. Alternatively, a pharmaceutical composition comprising at least one compound of the present application or a stereoisomer, tautomer, or solvate thereof can be administered to a subject who has been diagnosed with cancer.

In certain embodiments the compounds in accordance with the invention are administered to a subject with cancer in conjunction with other conventional cancer therapies such as radiation treatment or surgery. Radiation therapy is well known in the art and includes X-ray therapies, such as gamma-irradiation, and radiopharmaceutical therapies.

In certain embodiments the inventive Mnk inhibitor compounds are used with at least one anti-cancer agent. Anti-cancer agents include chemotherapeutic drugs. A chemotherapeutic agent includes, but is not limited to, an inhibitor of chromatin function, a topoisomerase inhibitor, a microtubule inhibiting drug, a DNA damaging agent, an antimetabolite (such as folate antagonists, pyrimidine analogs, purine analogs, and sugar-modified analogs), a DNA synthesis inhibitor, a DNA interactive agent (such as an intercalating agent), and a DNA repair inhibitor.

Illustrative chemotherapeutic agents include, without limitation, the following groups: anti-metabolites/anti-cancer agents, such as pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including natural products such as *vinca* alkaloids (vinblastine, vincristine, and vinorelbine), microtubule disruptors such as taxane (paclitaxel, docetaxel), vincristin, vinblastin, nocodazole, epothilones and navelbine, epidipodophyllotoxins (etoposide, teniposide), DNA damaging agents (actinomycin, amsacrine, anthracyclines, bleomycin, busulfan, camptothecin, carboplatin, chlorambucil, cisplatin, cyclophosphamide, Cytoxan, dactinomycin, daunorubicin, doxorubicin, epirubicin, hexamethylmelamineoxaliplatin, iphosphamide, melphalan, merchlorehtamine, mitomycin, mitoxantrone, nitrosourea, plicamycin, procarbazine, taxol, taxotere, temozolamide, teniposide, triethylenethiophosphoramide and etoposide (VP 16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (TNP470, genistein) and growth factor inhibitors (vascular endothelial growth factor (VEGF) inhibitors, fibroblast growth factor (FGF) inhibitors); angiotensin receptor blocker; nitric oxide donors; anti-sense oligonucleotides; antibodies (trastuzumab, rituximab); chimeric antigen receptors; cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin, irinotecan (CPT-11) and mitoxantrone, topotecan, irinotecan), corticosteroids (cortisone, dexamethasone, hydrocortisone, methylpednisolone, prednisone, and prenisolone); growth factor signal transduction kinase inhibitors; mitochondrial dysfunction inducers, toxins such as Cholera toxin, ricin, *Pseudomonas* exotoxin, *Bordetella pertussis* adenylate cyclase toxin, or diphtheria toxin, and caspase activators; and chromatin disruptors.

In certain embodiments an Mnk inhibitor in accordance with the present invention is used simultaneously, in the same formulation or in separate formulations, or sequentially with an additional agent(s) as part of a combination therapy regimen.

Mnk inhibitors according to the present application including their corresponding solvates and pharmaceutical compositions are also effective as therapeutic agents for treating or preventing cytokine mediated disorders, such as inflammation in a patient, preferably in a human. In one embodiment, a compound or composition in accordance with the invention is particularly useful for treating or preventing a disease selected from chronic or acute inflammation, chronic inflammatory arthritis, rheumatoid arthritis, psoriasis, COPD, inflammatory bowel disease, septic shock, Crohn's disease, ulcerative colitis, multiple sclerosis and asthma.

The inventive compounds, their corresponding solvates and pharmaceutically acceptable compositions are candidate therapeutics for treating brain related disorders which include without limitation autism, Fragile X-syndrome, Parkinson's disease and Alzheimer's disease. Treatment is effected by administering to a subject in need of treatment a compound of the present application, or a pharmaceutically acceptable composition thereof.

EXAMPLES

In the synthetic schemes described below, unless otherwise indicated all temperatures are set forth in degrees Celsius and all parts and percentages are by weight. Reagents are purchased from commercial suppliers and are used without further purification unless otherwise indicated. All solvents are purchased from commercial suppliers and are used as received.

The reactions set forth below are done generally under a positive pressure of nitrogen or argon at an ambient temperature (unless otherwise stated) in anhydrous solvents, and the reaction vessels are fitted with rubber septa (for flasks) or caps (for vials) for the introduction of substrates and reagents via syringe. Glassware is oven dried and/or heat dried. The reactions are assayed by TLC and/or analyzed by LC-MS and terminated as judged by the consumption of starting material. Occasionally, reactions are terminated early as desired products start to decompose.

Analytical thin layer chromatography (TLC) may be performed on glass-plates precoated with silica gel 60 $F_{254}$ 0.25 mm plates (EMD Chemicals), and visualized with UV light (254 nm) and/or iodine on silica gel and/or heating with TLC stains such as ethanolic phosphomolybdic acid, ninhydrin solution, potassium permanganate solution or ceric sulfate solution.

$^1$H-NMR spectra may be recorded on a Varian spectrometer operating at 400 MHz. NMR spectra are obtained as $CDCl_3$ solutions (reported in ppm), using chloroform as the reference standard (7.27 ppm for the proton and 77.00 ppm for carbon), $CD_3OD$ solutions using 3.4 ppm and 4.8 ppm as reference standards for the protons and 49.3 ppm as a reference standard for carbon, DMSO-$d_6$ (2.49 ppm for proton), or internally tetramethylsilane (0.00 ppm) when appropriate. Other NMR solvents are used as needed. When peak multiplicities are reported, the following abbreviations are used: s (singlet), d (doublet), t (triplet), q (quartet), m (multiplet), br (broadened), bs (broad singlet), dd (doublet of doublets), dt (doublet of triplets). Coupling constants, when given, are reported in Hertz (Hz).

The following examples are provided for purpose of illustration only.

Example 1: Synthetic Scheme for Crystalline Form A of 6'-((6-aminopyrimidin-4-yl)amino)-8'-methyl-2'H-spiro[cyclohexane-1,3'-imidazo[1,5-a]pyridine]-1',5'-dione (5)

Synthesis of Crystalline Form A of (5). 5-bromo-3-methyl-6-oxo-1,6-dihydropyridine-2-carboxamide (1) was combined with cyclohexanone in 1,4-dioxane. Sulfuric acid was added and the batch temperature is adjusted to 55° C. to 65° C. Typical reaction time was 1 hour. After completion, the batch temperature was adjusted to 10° C. to 30° C. and agitated for approximately 6 hours. The resulting solids were filtered, washed with water, and then dried under vacuum to give bromide (2) in an approximate yield of 92%.

Bromide (2) was combined with aminopyrimidine (3) with potassium carbonate, palladium (II) acetate, and 4,5-bis(diphenylphosphino)-9,9-dimethylxanthene (Xantphos) in 1,4-dioxane under nitrogen. The batch temperature was adjusted to 90° C. to 100° C. and stirred for approximately 18 hours. After completion, the temperature was adjusted to room temperature and then water was added. The resulting solid was filtered and then washed with methanol. The solids were slurried in methanol at 55° C. to 65° C. with optional seeding, cooled, filtered, and then dried under vacuum to afford cyclopropylpyrimidine (4) in an approximate yield of 98%.

Cyclopropylpyrimidine (4) was agitated with water, ethanol, and ethylenediamine and then treated with potassium hydroxide at 30° C. to 40° C. Agitation was continued until reaction was complete by HPLC. A second portion of potassium hydroxide was optionally added. Typical reaction time was 12 hours. The mixture was filtered and the filtrate was treated with hydrochloric acid until the pH was approximately 9 to afford 6-aminopyrimidine (5) as the free base.

6-aminopyrimidine (5) was returned to the reactor and suspended with aqueous ethanol at 35° C. to 45° C., cooled to room temperature, filtered, and then washed with ethanol. The wet cake was dried under vacuum to constant weight to afford Form A of 6'-((6-aminopyrimidin-4-yl)amino)-8'-methyl-2'H-spiro[cyclohexane-1,3'-imidazo[1,5-a]pyridine]-1',5'-dione (5) in an approximate yield of 79%. See FIG. 1 and Table 1.

Low solubilities of cyclopropylpyrimidine (4) and the free base of 6-aminopyrimidine (5) and the hydrochloric salt of (5) precluded the use of common solid-supported palladium scavenging agents (e.g., SILIAMETS® Thiol). The reaction mixture was homogenous after base hydrolysis of the cyclopropylamide (KOH in 1:1:1 THF/ethanol/water), where the use of ethylenediamine was surprisingly found to lower the palladium (II) levels to meet the permissible daily exposure limit based on the clinical dose. While earlier studies employed the use of activated carbon, this was unable to reduce the residual palladium levels to meet the permissible daily exposure limit based on the clinical dose.

A kinetic study identified ethanol as the solvent system for the final slurry step of the synthesis of Form A to ensure formation of the highly stable crystalline solid. For example, the free base of (5) was slurried at ambient temperature in various solvent systems, at various temperatures, with varying amounts of water. In each solvent condition, solids were isolated for XRPD analysis at 2, 4, 6, 24, and 72 hours. Equilibrium solubilities in these solvents were then calculated and used to identify ethanol for the final slurry step. The difference in free energy between solid phases with the same composition (i.e., polymorphs, hydrates, or solvates) is directly proportional to their relative solubilities. The most thermodynamically stable polymorph is Form A under the conditions examined.

TABLE 1

XRPD peak table for Form A of Compound (5)

| 2θ (deg) | Relative intensity (a.u.) |
|---|---|
| 8.07 | 27 |
| 10.81 | 44 |
| 12.00 | 7 |
| 12.37 | 5 |
| 13.79 | 3 |
| 14.68 | 26 |
| 15.39 | 4 |
| 16.19 | 1 |
| 16.69 | 15 |
| 17.34 | 11 |
| 18.89 | 8 |
| 20.26 | 7 |
| 21.15 | 1 |
| 21.30 | 2 |
| 21.77 | 8 |
| 22.07 | 100 |
| 22.84 | 2 |
| 23.49 | 2 |
| 24.40 | 1 |
| 24.90 | 1 |
| 25.34 | 3 |
| 25.75 | 1 |
| 26.12 | 2 |
| 26.54 | 4 |
| 27.16 | 10 |
| 27.48 | 1 |
| 28.06 | 5 |
| 28.76 | 13 |
| 29.04 | 1 |
| 29.26 | 1 |
| 29.59 | 2 |

Figure 2:
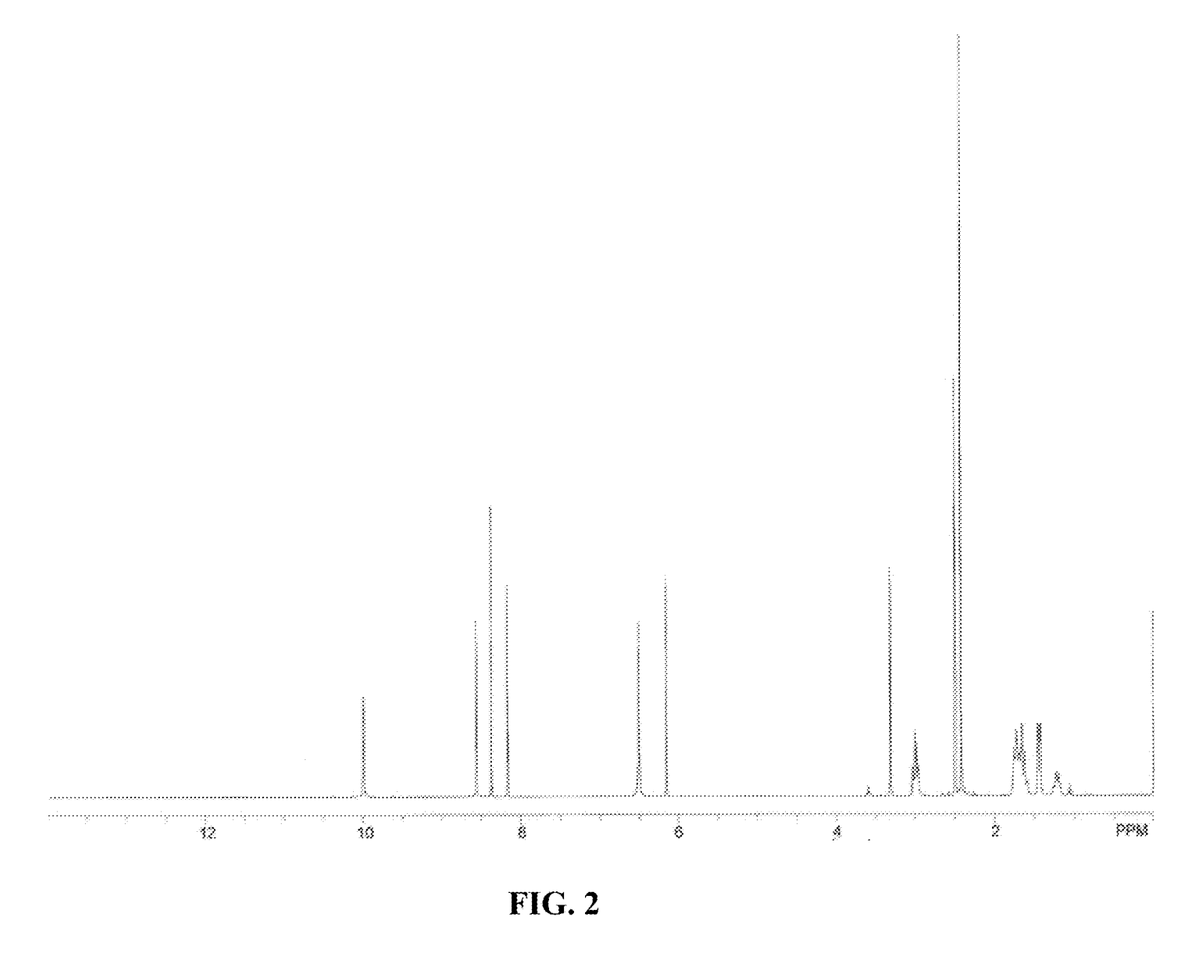
FIG. 2 shows the XRPD pattern of Form B of 6'-((6-aminopyrimidin-4-yl)amino)-8'-methyl-2'H-spiro[cyclohexane-1,3'-imidazo[1,5-a]pyridine]-1',5'-dione.

Synthesis of Crystalline Form B of (5). Using the free base of (5) as synthesized above, 6-aminopyrimidine (5) was suspended with a 39:61 (v/v) mixture of isopropanol/chloroform. The suspension was dried under a nitrogen gas purge to afford Form B of (5). See FIG. 2 and Table 2.

TABLE 2

XRPD peak table for Form B of Compound (5)

| 2θ (deg) | Relative intensity (a.u) |
|---|---|
| 6.31 | 6 |
| 8.78 | 100 |
| 9.31 | 15 |
| 12.15 | 10 |
| 12.67 | 3 |
| 13.30 | 3 |
| 15.90 | 6 |
| 16.45 | 8 |
| 17.01 | 17 |
| 17.31 | 8 |
| 17.63 | 7 |
| 17.79 | 15 |
| 18.71 | 4 |
| 18.97 | 15 |
| 19.84 | 16 |

TABLE 2-continued

XRPD peak table for Form B of Compound (5)

| 2θ (deg) | Relative intensity (a.u) |
|---|---|
| 20.22 | 11 |
| 21.49 | 22 |
| 22.55 | 11 |
| 23.23 | 8 |
| 23.96 | 12 |
| 26.28 | 10 |
| 26.59 | 5 |

Figure 3:
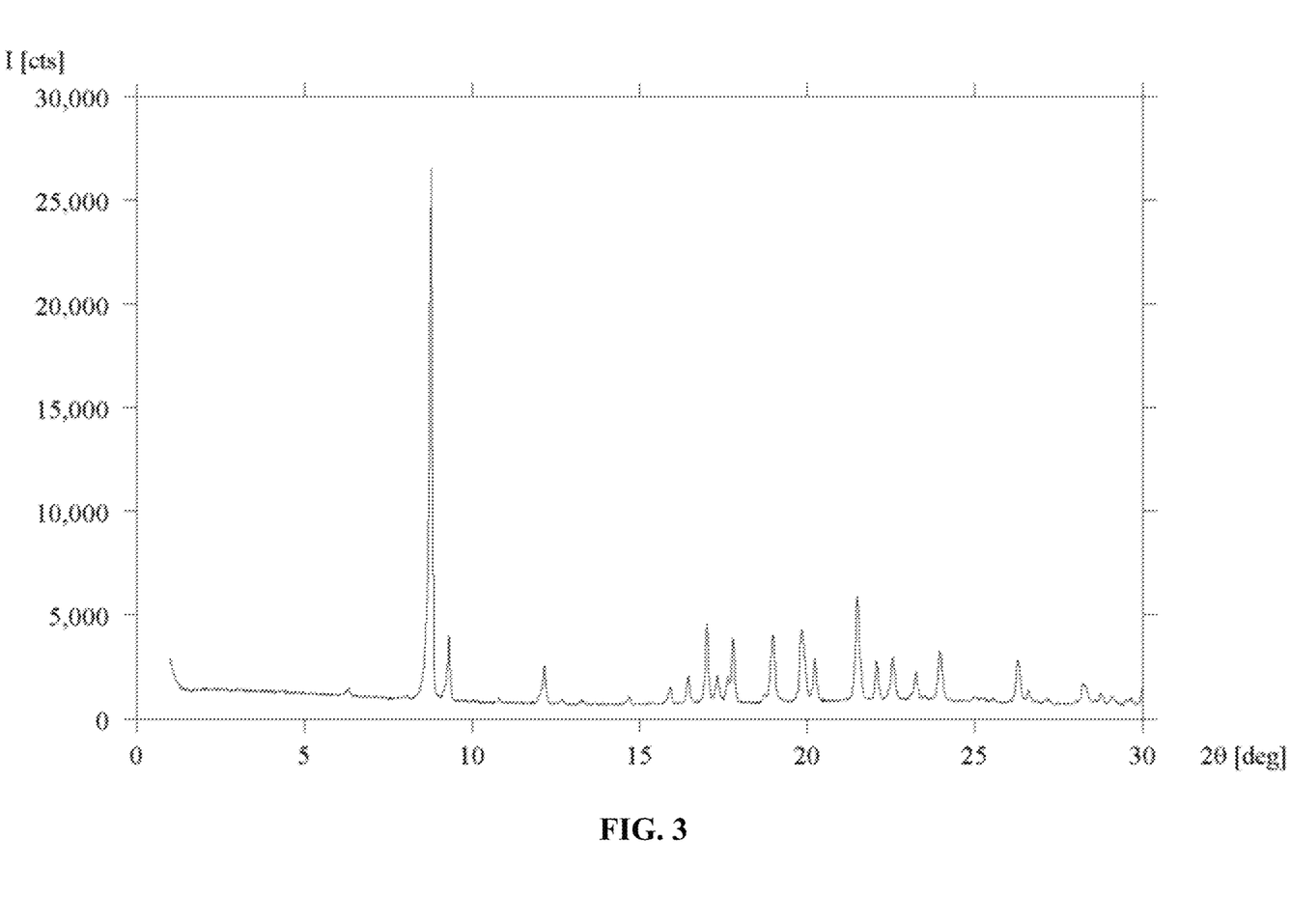
FIG. 3 shows the XRPD pattern of Form C of 6'-((6-aminopyrimidin-4-yl)amino)-8'-methyl-2'H-spiro[cyclohexane-1,3'-imidazo[1,5-a]pyridine]-1',5'-dione.

Synthesis of Crystalline Form C of (5). Using the free base of (5), 6-aminopyrimidine (5) in a sufficient amount was combined with ethylenediamine to afford a slurry. The slurry was sealed in a reactor and stirred at room temperature or at 40° C. for 4-5 days to afford Form C of Compound (5). Characterization data showed that Form C is a mono-solvate of ethylenediamine. See FIG. 3 and Table 3.

TABLE 3

XRPD peak table for Form C of Compound (5)

| 2θ (deg) | Relative intensity (a.u) |
|---|---|
| 6.98 | 45 |
| 7.58 | 83 |
| 10.03 | 54 |
| 10.59 | 18 |
| 14.93 | 46 |
| 16.32 | 61 |
| 16.68 | 8 |
| 19.04 | 37 |
| 19.95 | 21 |
| 20.13 | 23 |
| 20.87 | 17 |
| 21.07 | 13 |
| 21.43 | 29 |
| 22.81 | 12 |
| 24.94 | 10 |
| 25.37 | 13 |
| 25.85 | 100 |
| 26.98 | 52 |
| 27.59 | 12 |
| 27.80 | 18 |
| 28.21 | 8 |
| 28.83 | 6 |
| 29.78 | 8 |

Figure 4:
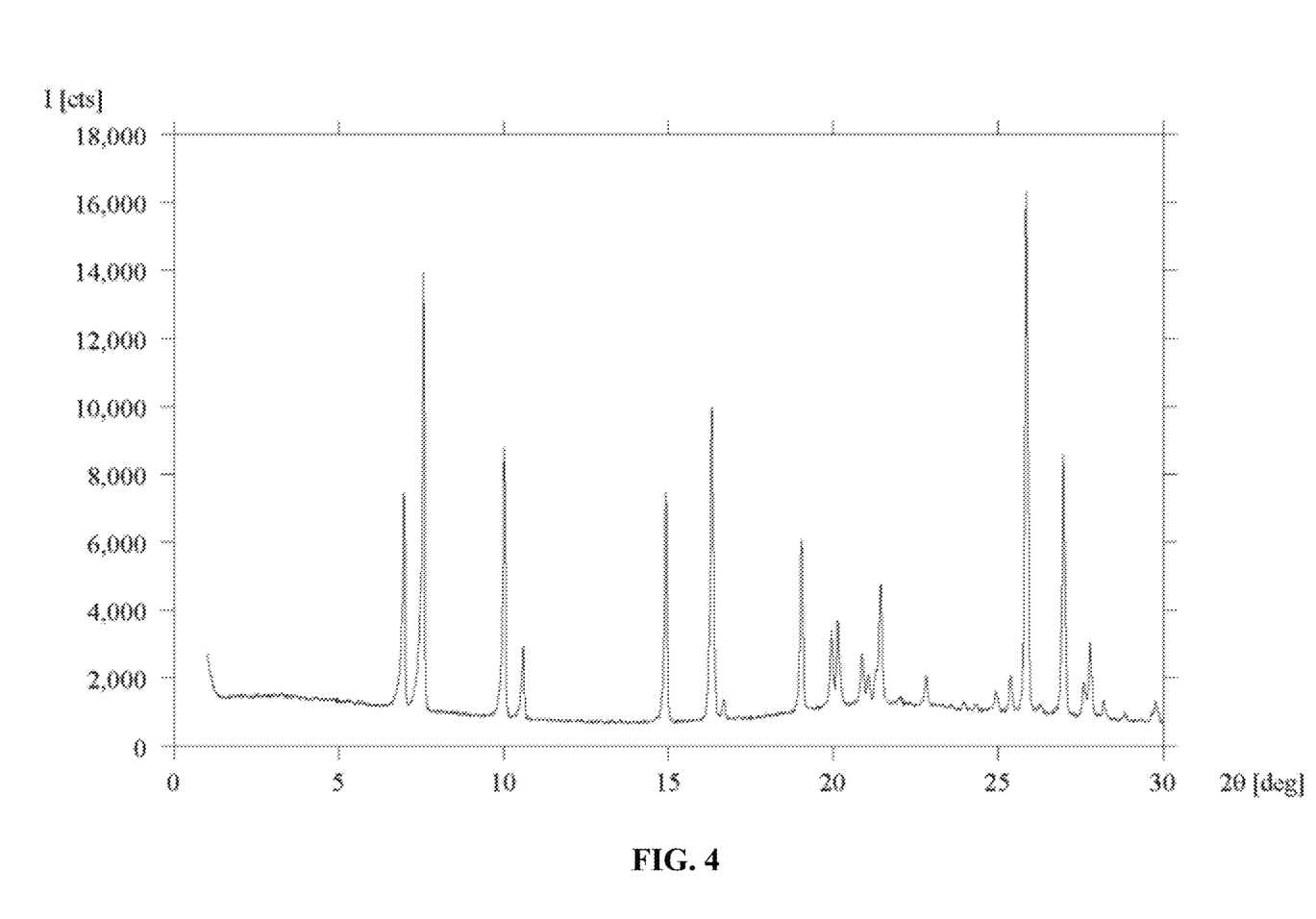
FIG. 4 shows the XRPD pattern of Form D of 6'-((6-aminopyrimidin-4-yl)amino)-8'-methyl-2'H-spiro[cyclohexane-1,3'-imidazo[1,5-a]pyridine]-1',5'-dione.

Synthesis of Crystalline Form D of (5). 6-aminopyrimidine (5) was combined with a 25:75 (v/v) solution of ethanol/hexafluoroisopropanol to afford a concentrated mixture in a small vial. The vial was uncapped and placed inside a sealed container containing ethanol as the anti-solvent. The sealed container was kept at ambient conditions until the presence of solids in solution was detected to provide Form D of (5). Characterization data showed that Form D is a hexafluoroisopropanol solvate. See FIG. 4 and Table 4.

TABLE 4

XRPD peak table for Form D of Compound (5)

| 2θ (deg) | Relative intensity (a.u) |
|---|---|
| 5.61 | 82 |
| 8.53 | 10 |
| 10.62 | 27 |
| 11.24 | 98 |

TABLE 4-continued

XRPD peak table for Form D of Compound (5)

| 2θ (deg) | Relative intensity (a.u) |
|---|---|
| 13.20 | 14 |
| 14.07 | 12 |
| 15.48 | 61 |
| 16.25 | 14 |
| 16.91 | 77 |
| 17.14 | 23 |
| 17.59 | 100 |
| 18.10 | 63 |
| 18.74 | 42 |
| 19.61 | 16 |
| 19.78 | 30 |
| 20.14 | 98 |
| 20.80 | 15 |
| 21.16 | 20 |
| 21.37 | 13 |
| 21.79 | 65 |
| 22.34 | 11 |
| 22.62 | 19 |
| 23.36 | 9 |
| 24.18 | 15 |
| 24.43 | 9 |
| 25.44 | 13 |
| 26.12 | 8 |
| 26.49 | 19 |
| 27.10 | 8 |
| 27.56 | 6 |
| 27.84 | 7 |
| 28.86 | 7 |
| 29.43 | 6 |

Example 2

Capsule Formulation of Form A

Referring to Table 5, a pharmaceutical composition comprising crystalline solids of the present application may include pharmaceutically acceptable carriers, diluents, and/or excipients. In a non-limiting embodiment, the composition comprises Form A of (5), a disintegrant, a filler, a lubricant, and a glidant. It was found that the microionization of the free base including excipients provided a capsule formulation with unexpected stability versus the hydrochloric acid salt of (5) as a powder-in-bottle formulation.

TABLE 5

Capsule Formulation of Form A of Compound (5)

| Component | Function | Quantity (mg/unit dose) |
|---|---|---|
| Compound 5 | Active Ingredient | 100.0 |
| Avicel PH200 (microcrystalline cellulose) | Filler | 99.7 |
| Citric acid | Disintegrant | 34.3 |
| Sodium bicarbonate | Disintegrant | 45.0 |
| Sodium lauryl sulfate | Lubricant | 15.0 |
| Aerosol 200 (fumed silica) | Glidant | 3.0 |
| Magnesium stearate | Lubricant | 3.0 |

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A process of producing a compound having the structure, the process comprising;

a) reacting compound (1), with cyclohexanone and sulfuric acid to produce compound (2), b) reacting compound (2) with compound (3), in the presence of Pd(OAc)₂ and potassium carbonate to produce compound (4)

(4)

c) reacting compound (4) with ethylenediamine and potassium hydroxide to produce compound (5)

(5)

2. A process of producing a crystalline solid of a compound having the structure:

wherein the crystalline solid is characterized by an X-ray powder diffraction pattern comprising peaks, expressed in values of degrees 2θ, at about 8.07; about 10.81; about 14.68; and about 22.07±0.2, the process comprising
a) creating a suspension of the compound in aqueous ethanol at 35° C. to 45° C.

b) cooling the suspension to room temperature
c) filtering the suspension to isolate a cake of crystalline solid
d) washing the cake with aqueous ethanol, and
e) drying the cake under vacuum to constant weight.

3. A solid pharmaceutical composition comprising a therapeutically effective amount of a crystalline solid of a compound having the structure:

and a pharmaceutically acceptable particulate carrier, wherein the crystalline solid of the compound is characterized by an X-ray powder diffraction pattern comprising peaks, expressed in values of degrees 2θ, at about 8.07; about 10.81; about 14.68; and about 22.07±0.2.

4. The solid pharmaceutical composition of claim 3, wherein the crystalline solid of the compound is characterized by an X-ray powder diffraction pattern comprising peaks, expressed in values of degrees 2θ, at about 8.07; about 10.81; about 14.68; about 16.69; about 17.34; and about 22.07±0.2.

5. The solid pharmaceutical composition of claim 3, wherein the crystalline solid of the compound is characterized by an X-ray powder diffraction pattern comprising-peaks, expressed in values of degrees 2θ, at about 8.07; about 10.81; about 12.00; about 12.37; about 13.79; about 14.68; about 15.39; about 16.19; about 16.69; about 17.34; about 18.89; about 20.26; about 21.15; about 21.30; about 21.77; about 22.07; about 22.84; about 23.49; about 24.40; about 24.90; about 25.34; about 25.75; about 26.12; about 26.54; about 27.16; about 27.48; about 28.06; about 28.76; about 29.04; about 29.26; and about 29.59±0.2.

6. The solid pharmaceutical composition of claim 3, wherein the crystalline solid is characterized by an X-ray powder diffraction pattern substantially as shown in FIG. 1.

\* \* \* \* \*